United States Patent
Vachon et al.

(10) Patent No.: US 6,642,015 B2
(45) Date of Patent: Nov. 4, 2003

(54) HYDROPHILIC POLYMERIC MATERIAL FOR COATING BIOSENSORS

(75) Inventors: David J. Vachon, Granada Hills, CA (US); Brooks B. Cochran, Sylmar, CA (US); Bill C. Ponder, Valencia, CA (US)

(73) Assignee: MiniMed Inc., Northridge, CA (US)

( * ) Notice: Subject to any disclaimer, the term of this patent is extended or adjusted under 35 U.S.C. 154(b) by 0 days.

(21) Appl. No.: 09/753,095

(22) Filed: Dec. 29, 2000

(65) Prior Publication Data

US 2002/0123087 A1 Sep. 5, 2002

(51) Int. Cl.[7] .............. C12Q 1/54; B32B 9/04; B32B 27/40
(52) U.S. Cl. ............ 435/14; 428/447; 428/423.1; 528/17; 528/28; 528/38; 528/44; 528/76
(58) Field of Search ............ 528/17, 28, 38, 528/44, 76; 204/403.11; 428/447, 423.1

(56) References Cited

U.S. PATENT DOCUMENTS

| | | | |
|---|---|---|---|
| 5,045,391 A | * | 9/1991 | Brandt et al. .............. 428/336 |
| 5,290,615 A | * | 3/1994 | Tushaus et al. .............. 427/387 |
| 5,322,063 A | | 6/1994 | Allen et al. |
| 5,777,060 A | | 7/1998 | Van Antwerp |
| 5,786,439 A | | 7/1998 | Van Antwerp et al. |
| 5,882,494 A | * | 3/1999 | Van Antwerp ......... 204/403.11 |
| 5,965,380 A | | 10/1999 | Heller et al. |
| 6,355,759 B1 | * | 3/2002 | Sherman et al. .............. 528/28 |

FOREIGN PATENT DOCUMENTS

| | | |
|---|---|---|
| JP | 62 102816 A | 5/1987 |
| WO | WO 98/13685 | 4/1998 |

OTHER PUBLICATIONS

Technical Bulletin for Jeffamine D–2000.*

* cited by examiner

Primary Examiner—Robert Dawson
Assistant Examiner—Marc S Zimmer
(74) Attorney, Agent, or Firm—Gates & Cooper LLP (57) ABSTRACT

Disclosed is a biocompatible membrane comprising a hydrophilic polyurea composition. The hydrophilic polyurea composition comprises the product of a reaction mixture comprising (a) an amino terminated polysiloxane, (b) a hydrophilic polymer selected from the group consisting of a diamino terminated copolymer of polypropylene glycol and polyethylene glycol, polyethylene glycol, polypropylene glycol and diamino polyethylene glycol having an average molecular weight of from about 400 to about 2000, and (c) a diisocyanate selected from the group consisting of hexamethylene-1,6-diisocyanate, dicyclohexylmethane 4,4'-diisocyanate, and isophorone diisocyanate, and constituting about 50 mole % of the reaction mixture. In this mixture, (a) and (b) constitute a polymeric portion of the reaction mixture, and the hydrophilic polyurea composition has a ratio of its diffusion coefficient for oxygen to its diffusion coefficient for glucose of from about 2,000 to about 10,000. Also provided are biosensors coated with a membrane of the invention, and methods of using such biosensors to measure an analyte in a tissue of a subject.

31 Claims, 1 Drawing Sheet

Figure 1

HYDROPHILIC POLYMERIC MATERIAL FOR COATING BIOSENSORS

TECHNICAL FIELD OF THE INVENTION

This invention relates generally to polymeric materials and to methods of making and using such materials. The polymeric materials are hydrophilic, biocompatible, and suitable for use with biosensors, such as glucose sensors.

BACKGROUND OF THE INVENTION

Biosensors are small devices that use biological recognition properties for selective detection of various analytes or biomolecules. Typically, the sensor will produce a signal that is quantitatively related to the concentration of the analyte. To achieve a quantitative signal, a recognition molecule or combination of molecules is often immobilized at a suitable transducer, which converts the biological recognition event into a quantitative response.

The need for the continuous monitoring of biological markers (analytes) in medicine has sparked a tremendous interest in the study of biosensors in recent years. Without question, the greatest interest has been geared toward the development of sensors to detect glucose. In particular, enzymatic (amperometric) glucose electrodes have been studied in more detail than any other biosensors. Electroenzymatic biosensors use enzymes to convert a concentration of analyte to an electrical signal. Immunological biosensors rely on molecular recognition of an analyte by, for example, antibodies. Chemoreceptor biosensors use chemoreceptor arrays such as those of the olfactory system or nerve fibers from the antennules of the blue crab *Callinectes sapidus* to detect the presence of amino acids in concentrations as low as $10^9$ M. For a review of some of the operating principles of biosensors, see Bergveld, et al., Advances in Biosensors, Supplement 1, p. 31–91, Turner ed., and Collison, et al., Anal. Chem. 62:425–437 (1990).

Regardless of the type of biosensor, each will possess certain properties to function in vivo and provide an adequate signal. First, the elements of the biosensor should be compatible with the tissue to which it is attached, and be adequately safe such that allergic or toxic effects ate not exerted. Further, the sensor should be shielded from the environment to control drift in the generated signal. Finally, the sensor should accurately measure the analyte in the presence of proteins, electrolytes and medications, which may have the potential to interfere.

The biosensor of interest is an amperometric glucose sensor. There are several reasons for the wide-ranging interest in glucose sensors. In the healthcare arena, enzymatic glucose test strips ate useful for monitoring the blood sugar of patients with diabetes mellitus. A sensor that has the ability to continuously monitor the blood, or interstitial glucose of a person with diabetes could provide great insight into the level of control that they have over their disease and avoid the need for repeated blood draws. Additionally, a continuously monitoring glucose sensor is one of the critical components necessary for the development of an artificial pancreas. To make such a system possible, a reliable glucose sensor must communicate with an insulin pump.

An additional commercial application of this technology focuses on sensors that can be used to monitor fermentation reactions in the biotechnology industry. From a scientific and commercial standpoint, interest has grown beyond glucose to other analytes for the diagnosis of numerous medical conditions other than diabetes.

Amperometric glucose sensors and oxido-reductase enzymes that use $O_2$ as a co-substrate, and are designed for subcutaneous or intravenous use, typically require both an outer membrane and an anti-interference membrane. The necessity for two distinct membranes is largely due to the fundamental nature of the sensor, as well as the environment in which the measurement is made.

A glucose sensor works by a reaction in which glucose reacts with oxygen in the presence of glucose oxidase (GOd) to form gluconolactone and hydrogen peroxide. The gluconolactone further reacts with water to hydrolyze the lactone ring and produce gluconic acid. The $H_2O_2$ formed is electrochemically oxidized at an electrode as shown below (Equation 1):

$$H_2O_2 \rightarrow O_2 + 2e^- + 2H^+ \qquad (I)$$

The current measured by the sensor/potentiostat (+0.5 to +0.7 v oxidation at Pt black electrode) is the result of the two electrons generated by the oxidation of the $H_2O_2$. Alternatively, one can measure the decrease in the oxygen by amperometric measurement 0.5 to −1 V reduction at a Pt black electrode).

The stoichiometry of the GOd reaction points to a challenge of developing a reliable glucose sensor. If oxygen and glucose are present in equimolar concentrations, then the $H_2O_2$ is stoichiometrically related to the amount of glucose that reacts at the enzyme. In this case, the ultimate current is also proportional to the amount of glucose that reacts with the enzyme. If there is insufficient oxygen for all of the glucose to react with the enzyme, then the current will be proportional to the oxygen concentration, not the glucose concentration. For the sensor to be a true glucose sensor, glucose must be the limiting reagent, i.e. the $O_2$ concentration must be in excess for all potential glucose concentrations. For example, the glucose concentration in the body of a diabetic patient can vary from 2 to 30 mM (millimoles per liter or 36 to 540 mg/dl), whereas the typical oxygen concentration in the tissue is 0.02 to 0.2 mM (see, Fisher, et al., Biomed. Biochem. Acta. 48:965–971 (1989). This ratio in the body means that the sensor would be running in the Michaelis Menten limited regime and would be very insensitive to small changes in the glucose concentration. This problem has been called the "oxygen deficit problem". Accordingly, a method or system must be devised to either increase the $O_2$ in the GOd enzyme layer, decrease the glucose concentration, or devise a sensor that does not use $O_2$.

There is a need for a glucose sensor having a biocompatible membrane with an improved ratio of its oxygen permeability to it glucose permeability, and that offers physical and biological stability and strength, adhesion to the substrate, processibility (i.e. solubility in common organic solvents for the development of coatings from polymer lacquer and the ability to cut using laser ablation or other large scale processing method), the ability to be synthesized and manufactured in reasonable quantities and at reasonable prices, and compatibility with the enzyme as deposited on the sensor. The present invention fulfills these needs and provides other related advantages.

SUMMARY OF THE INVENTION

The invention provides a biocompatible membrane comprising a hydrophilic polyurea composition. The hydrophilic polyurea composition comprises the product of a reaction mixture comprising (a) an amino terminated polysiloxane, (b) a hydrophilic polymer selected from the group consisting of a diamino terminated copolymer of polypropylene glycol and polyethylene glycol, polyethylene glycol, polypropylene glycol and diamino polyethylene glycol having an average molecular weight ($M_D$) of from about 400 to about 2000, and (c) a diisocyanate selected from the group consisting of hexamethylene-1,6-diisocyanate, dicyclohexylmethane 4,4'-diisocyanate, and isophorone diisocyanate, and constituting about 50 mole % of the reaction mixture. In this mixture, (a) and (b) constitute a polymeric portion of the reaction mixture, and when the mixture is reacted with (c), the end product polymer has a ratio of its diffusion coefficient for oxygen to its diffusion coefficient for glucose of from about 2,000 to about 10,000. In a preferred embodiment, the hydrophilic polyurea composition has a ratio of its diffusion coefficient for oxygen to its diffusion coefficient for glucose of from about 3,000 to about 7,000. In a more preferred embodiment, the hydrophilic polyurea composition has a ratio of its diffusion coefficient for oxygen to its diffusion coefficient for glucose of from about 5,000 to about 7,000.

The biocompatible membrane of the invention can include a hydrophilic polymer that comprises a polypropylene glycol)-block-poly(ethylene glycol) bis(2-aminopropyl ether). The polysiloxane preferably has a molecular weight of about 500 to about 3,500, and most preferably, about 2,500. In some embodiments, the reaction mixture further comprises a chain extender, such as N-methyl diethanolamine, ethylene diamine, butane diol, diethylene glycol, propane diol or water. The biocompatible membrane of the invention can be the product of a mixture having a glucose diffusion coefficient of from about $1 \times 10^{-9}$ $cm^2/s$ to about $200 \times 10^{-9}$ $cm^2/s$ at 37° C., or preferably, from about $2.5 \times 10^{-9}$ $cm^2/s$ to about $10 \times 10^{-9}$ $cm^2/s$ at 37° C.

In a preferred embodiment, the polysiloxane content is from about 15 mole percent to about 75 mole percent of the polymeric portion of the mixture, or more preferably, about 50 mole percent of the polymeric portion of the mixture. In one embodiment, the hydrophilic polymer comprises a combination of a diamino terminated copolymer of polypropylene glycol and polyethylene glycol having an average molecular weight of about 600 and a diamino terminated copolymer of polypropylene glycol and polyethylene glycol having an average molecular weight of about 900. In another embodiment, the polymeric portion of the mixture comprises about 50 mole percent polysiloxane, about 25 mole percent hydrophilic polymer having an average molecular weight of about 600, and about 25 mole percent hydrophilic polymer having an average molecular weight of about 900. Preferably, the hydrophilic polymer comprises a diamino terminated copolymer of polypropylene glycol and polyethylene glycol. A preferred diamino terminated copolymer of polypropylene glycol and polyethylene glycol is poly(propylene glycol)-block-poly(ethylene glycol) bis(2-aminopropyl ether).

The invention further provides an implantable biosensor for measuring an analyte in biological tissue, the biosensor having a coating comprising a biocompatible membrane of the invention. The implantable biosensor can further comprise a transducer that generates a signal upon contact with the analyte. In a preferred embodiment, the analyte is glucose and the transducer is glucose oxidase.

The invention additionally provides a method of measuring an analyte in a tissue of a subject. The method comprises introducing an implantable biosensor of the invention into the tissue of the subject, and detecting the signal generated by the transducer. The amount of signal corresponds to the amount of analyte. Preferably, the analyte is glucose and the transducer is glucose oxidase.

DETAILED DESCRIPTION

Figure 1:
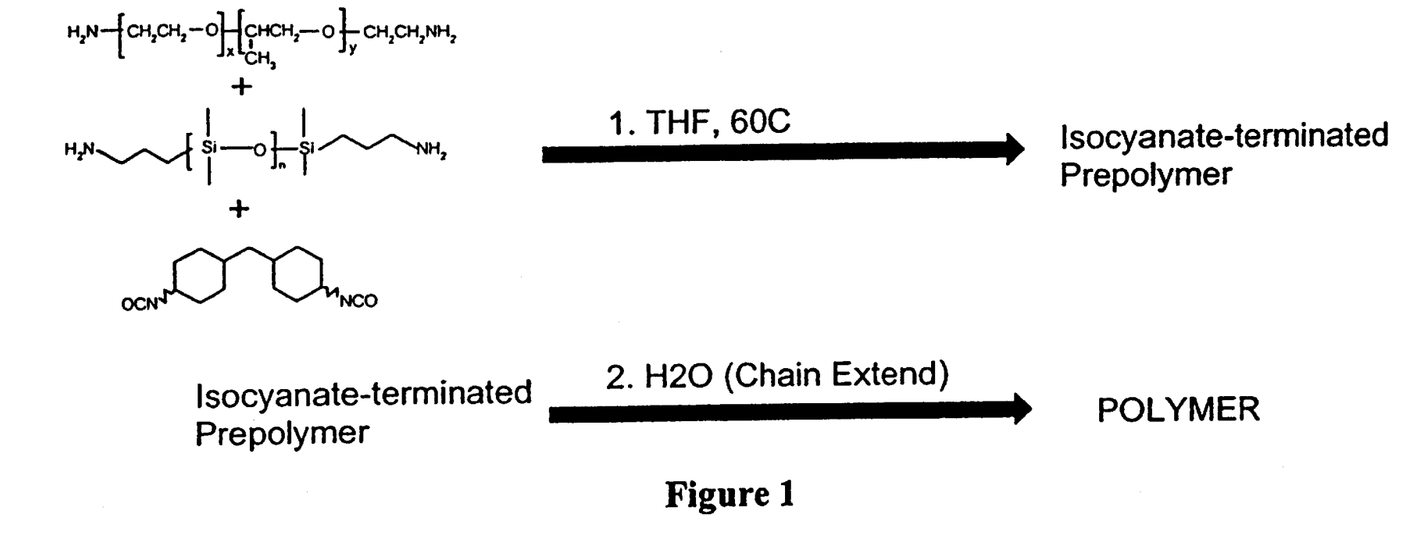
FIG. 1 is a schematic illustration of polymer formation using water as a chain extender and starting with a polyol diamine, a polysiloxane diamine and hexamethylene diisocyanate.

All scientific and technical terms used in this application have meanings commonly used in the art unless otherwise specified. As used in this application, the following words or phrases have the meanings specified.

As used herein, the term "polyurea" refers to a polymer containing urea linkages. Such polymers may additionally contain urethane linkages. Typically, such polymers are formed by combining diisocyanates with amines and/or alcohols. For example, combining isophorone diisocyanate with PEG 600 and aminopropyl polysiloxane under polymerizing conditions provides a polyurethane/polyurea composition having both urethane (carbamate) linkages and urea linkages.

As used herein, "adhered to" or "adhered thereto" means stuck to or fused with such that a substance adhered to a surface remains substantially attached to or closely associated with the surface.

As used herein, "a" or "an" means at least one, and unless clearly indicated otherwise, includes a plurality.

Overview

The invention provides hydrophilic glucose limiting polymeric materials that offer improved hydration and faster response times. The superior hydration characteristics of the polymeric materials provide improved biocompatibility and resistance to biofouling. The increased hydrophilicity of the material provides a polymer that can be coated onto a biosensor without requiring a second coating to enhance surface wetting of the device. In addition, the invention offers polymeric materials whose overall polymeric structure can be controlled by use of a diamine or diol chain extender instead of water. The invention additionally provides polymer blends that offer advantageous features over individual polymeric materials that can be selected in accordance with desired characteristics. Also provided are biosensors having a biocompatible membrane of the invention adhered thereto, and methods of measuring an analyte in a tissue of a subject using such a biosensor.

Three characteristics of the biocompatible membranes of the invention that are of particular interest are glucose permeability, oxygen permeability, and the thermal dependence of these permeabilities. A preferred membrane has a permeability constant for glucose mass transport through the material that approximates $5.0 \times 10^{-9}$ $cm^2/s$ at 37° C. Additionally, a ratio of oxygen permeability to glucose permeability of greater than about 3000 is preferred. Generally, the higher the permeability ratio, the better, with the exception of a ratio of infinity, which would result from a glucose permeability approaching zero. Also preferred is a membrane that exhibits minimal change in oxygen and glucose permeability in response to temperature changes.

Biocompatible Membranes

A glucose sensor intended for in vivo use requires that the supply of oxygen in the vicinity of the sensing element not be depleted. Additionally, the glucose should diffuse to the sensor at a controlled rate. Overall, the membrane should control the relative rates of diffusion of oxygen and glucose to the sensor so that the local concentration of oxygen is not depleted. Additionally, glucose sensors intended for in vivo use must also be biocompatible with the body, and they must be able to function in an environment in which harsh inflammatory components brought on by the process of tissue injury and healing are present. Furthermore, these membranes must resist against the adhesion of biological components (biofouling) such as cells and proteins that can interfere with a sensor's performance. Thus, the enzyme(s) used in such sensors must be protected from degradation or denaturation, while the elements of such sensors must be protected from molecules that would foul the sensors or their accuracy will decrease over time.

In one aspect, the present invention provides a biocompatible membrane comprising a hydrophilic polyurea composition. The hydrophilic polyurea composition comprises the product of a reaction mixture comprising (a) an amino terminated polysiloxane, (b) a hydrophilic polymer selected from the group consisting of a diamino terminated copolymer of polypropylene glycol and polyethylene glycol, polyethylene glycol, polypropylene glycol and diamino polyethylene glycol having an average molecular weight of from about 400 to about 2000, and (c) a diisocyanate selected from the group consisting of hexamethylene-1,6-diisocyanate, dicyclohexylmethane 4,4'-diisocyanate, and isophorone diisocyanate, and constituting about 50 mole % of the reaction mixture. In this mixture, (a) and (b) constitute a polymeric portion of the reaction mixture, and the hydrophilic polyurea composition has a ratio of its diffusion coefficient for oxygen to its diffusion coefficient for glucose of from greater than 2,000 to about 10,000. In a preferred embodiment, the hydrophilic polyurea composition has a ratio of its diffusion coefficient for oxygen to its diffusion coefficient for glucose of from about 3,000 to about 7,000. In a more preferred embodiment, the hydrophilic polyurea composition has a ratio of its diffusion coefficient for oxygen to its diffusion coefficient for glucose of from about 5,000 to about 7,000. The biocompatible membrane of the invention can be the product of a mixture having a glucose diffusion coefficient of from about $1 \times 10^{-9}$ cm$^2$/s to about $200 \times 10^{-9}$ cm$^2$/s at 37° C., or preferably, from about $2.5 \times 10^{-9}$ cm$^2$/s to about $10 \times 10^{-9}$ cm$^2$/s at 37° C.

Polymer Blends

The biocompatible membrane of the invention comprises a combination of hydrophobic (polysiloxane) and hydrophilic polymers. In a preferred embodiment, the hydrophilic polymer comprises polyurea (see, e.g., U.S. Pat. Nos. 5,777, 060 and 5,786,439, both of which are incorporated herein by reference) and, optionally, polyurethane as well. The membrane preferably includes a blend of two or more polymers, each of which can comprise a combination of two or more polymers with different characteristics, including combinations of hydrophobic and hydrophilic polymers, yielding a solid mixture or blend with desired glucose limiting and performance properties.

In one embodiment, the hydrophilic polymer comprises a diamino terminated copolymer of polypropylene glycol and polyethylene glycol. A preferred diamino terminated copolymer of polypropylene glycol and polyethylene glycol, comprises polypropylene glycol)-block-poly(ethylene glycol) bis(2-aminopropyl ether). Suitable hydrophilic polymers for use in polymer blends of the invention have average molecular weights in the range of from about 400 to about 2000, and include poly(propylene glycol)-block-poly(ethylene glycol) bis(2-aminopropyl ether)s Jeffamine™; Huntsman Chemical) such as Jeffamine 600 (J600), having an average molecular weight (mw) of 600,and Jeffamine 900 (J900), having an average mw of 900; polyethylene glycols (PEGs), such as PEG having an average mw of 600, 1000 or 2000 (PEG 600, PEG 1000, PEG 2000); polypropylene glycols (PPGs), such as PPG having an average mw of 400; and diamino polyethylene glycol (DAPEG), such as DAPEG 2000, having an average mw of 2000.

In a preferred embodiment, the polysiloxane content is from about 15 mole % to about 75 mole % of the polymeric portion of the mixture, or more preferably, about 50 mole % of the polymeric portion of the mixture. A preferred polysiloxane has a molecular weight of about 500 to about 3,500, with a molecular weight of about 2,500 being most preferable. In one embodiment, the hydrophilic polymer comprises a combination of J600 and J900. In another embodiment, the polymeric portion of the mixture comprises about 50 mole % polysiloxane, about 25 mole % hydrophilic polymer having an average molecular weight of about 600, and about 25 mole % hydrophilic polymer having an average molecular weight of about 900. Preferably, the hydrophilic polymer comprises a diamino terminated copolymer of polypropylene glycol and polyethylene glycol, such as poly (propylene glycol)-block-poly (ethylene glycol) bis(2-aminopropyl ether) (Jeffamine™). Exemplary polymeric compositions for use in the reaction mixture of the invention and their permeability characteristics are described in Table 1 (wherein "hp" refers to hydrophilic portion). Additional preferred polymer combinations and their influence on sensor characteristics are described in Table 2.

TABLE 1

| Designation | Composition | Hydration | | Diffusion Coefficient | Intrinsic | nA | Signal Min– | | Thickness |
| | | Initial Rate (mg/min) | % Max | (mm*h) × 10e$^{-6}$ | Viscosity (mL/g) | @ 100 mg/dL | Max (nA) | R$^2$ | ness (μm) |
|---|---|---|---|---|---|---|---|---|---|
| | 75/25 J600/PS510 | 29 | 37 | 0.82 | 30 | 25–39 | 22–62 | 0.997–0.999 | 2.7 |
| 936-53 | 85/15 J600/PS510 | 52.5 | 46 | 1.64 | 20 | 70.1 | 59–105 | 0.998 | 1.6 |
| 936-11 | hp-75/25 J600/P600 | 23 | 32 | 0.59 | 35 | 39.2 | 35.5–42.4 | 1 | 3.8 |
| 936-15 | hp-100J900 | 97 | 54 | 15.5 | 50 | 195.8 | 149–236 | 0.974 | 2.3 |
| 936-22 | hp-75/25 J600/J900 | 28.5 | 43 | 2.76 | 38 | 64 | 60.7–71.5 | 0.999 | 3.6 |
| 936-42 | hp-90/10 | 68.5 | 35 | 1.7 | 21 | 42.8 | 39.1– | 0.998 | 2.8 |

TABLE 1-continued

| Designation | Composition | | | | | | | | |
|---|---|---|---|---|---|---|---|---|---|
| 985-67 | J600/J900 hp-85/15 | 58 | 42 | 1.67 | 26 | 68.6 | 47.1 65–72 | 0.999 | 2.2 |
| 985-23 | J600/J900 35/20/45 | 11 | 5 | 0.24 | 46 | 23.6 | 23.3–24.1 | 1 | 2.6 |
| 985-79 | J600/J900/PS510 75/25 J600/PS510 w/EDA Extension | 51.5 | 38 | 1.33 | 16 | 49.2 | 43.5–56.6 | 0.997 | 1.9 |
| | 2% Blend of 75/25 J600/PS510 w/ hp-100J900 | 49 | 30 | 1.09 | N/A | 36.1 | 29.9–46.1 | 0.999 | 2.5 |
| | 5% Blend | 56.5 | 31.6 | 1.56 | N/A | 54.2 | 42.3–76.6 | 0.999 | 2.1 |
| | 11% Blend | 62 | 31.9 | 1.32 | N/A | 49 | 44–55 | 0.998 | 2.2 |
| | 15% Blend | 60 | 37.3 | 1.52 | N/A | 58.8 | 54–62 | 0.998 | 2.3 |
| | 20% Blend | 65 | 36.7 | 1.92 | N/A | 57.6 | 32.4–69.9 | 0.993 | 2.3 |
| 1001-39 | 50/50 DAPEG2000/PS510 | 280.9 | 52 | 38.4 | 36 | | | | |
| | 2% Blend of 75/25 J600/PS510 w/ 1/1 DAPEG2000/PS510 | 51 | 28.5 | | | 36.3 | 34–40 | 1 | 2.6 |
| | 5% Blend | 54 | 21.5 | | | 43.5 | 41–45 | 0.999 | 2.5 |
| | 15% Blend | 58 | 11.7 | | | 61.9 | 58–67 | 0.999 | 2.5 |
| 927-34(76) | hp:50% peg600 | 15 | 37 | 0.06 | 46 | 12 | 10 to 14 | 0.999 | 1.8 |
| 927-40 | hp:50% peg1000 | 77 | 98 | 9.23 | 39 | 103 | 100 to 108 | 0.997 | uneven |
| 927-43 | hp:50% jeff900 | 60 | 47 | 3.88 | 40 | 136 | 117 to 151 | 0.993 | 1.8 |
| 927-48 | 80% jeff600 | 52 | 39 | 2.32 | 23 | 32 | 28 to 35 | 0.998 | 2.5 |
| 927-52 | hp:25% ppg400 | 24 | 21 | 0.54 0.47 | 31 | 26 | 23 to 33 | 0.999 | 1.7 |
| 927-54 | hp:50% ppg400 | 10 | 12 | 0.04 | 23 | 6 | 7 to 32 | 0.978 | 4.1 |
| 986-17 | 65% jeff600 | 22 | 20 | 0.22 | 32 | 18 | 17 to 20 | 0.999 | 3.2 |
| 986-49 | nmda/ extension | 38 | 29 | 0.79 | 27 | 24 | 23 to 25 | 0.999 | 2.9 |
| 986-63 | 10% excess hmdi | 42 | 31 | 0.79 | 20 | 26 | 25 to 35 | 0.998 | 3.4 |

| | Composition | Theta (air) | | | Theta (AI) | | |
|---|---|---|---|---|---|---|---|
| Designation | Production Material | Dry | Hydrated | Post-hydration | Dry | Hydrated | Post-hydration |
| 936-53 | 85/15 J600/PS510 | 109.1 | 97.9 | 106.8 | 113.1 | 95.3 | 104.2 |
| 936-11 | hp-75/25 J600/P600 | 100.1 | 98.6 | 107.8 | 103.4 | 105.3 | 109.8 |
| 936-15 | hp-100J900 | | | | | | |
| 936-22 | hp-75/25 J600/J900 | | | | | | |
| 936-42 | hp-90/10 J600/J900 | | | | | | |
| 985-67 | hp-85/15 J600/J900 | 103.9 | 106.2 | 105 | 112 | 109.1 | 108.7 |
| 985-23 | 35/20/45 J600/J900/PS510 | 93.6 | | | 105.4 | | |
| 985-79 | Production Ration w/ EDA Extension 2% Blend of Production w/hp- 100 | 108.1 | 105.9 | | 111.4 | 106.2 | |

TABLE 1-continued

|  |  |  |  |  |  |  |
|---|---|---|---|---|---|---|
| J900 5% Blend | | | | | | |
| 11% Blend | | | | | | |
| 15% Blend | | | | | | |
| 20% Blend | 107.2 | 105.2 | | 93.8 | 102.7 | |
| 1001-39 50/50 DAPEG2000/PS510 | 109.1 | 79.3 | 105.4 | 103.5 | 51.2 | 105.4 |

TABLE 2

| Polymer | Membrane Composition | | | Oxygen Permeability (cm²/s) x $10^{-5}$ | Glucose Permeability (cm²/s) x $10^{-9}$ | $O_2$/Glucose Permeability Ratio | Percent Change in Glucose Permeability from 37° C. | |
|---|---|---|---|---|---|---|---|---|
| | Polysiloxane | Jeff 900 | Jeff 600 | | | | 27° C. (high) | 42° C. (low) |
| A | 50% | 50% | | 2.9 | 27 | 1074 | 18% | −19% |
| B | 50% | | 50% | 2.0 | Below detection limit | N/A | | |
| C | 50% | 25% | 25% | 2.3 | 4.4 | 5227 | 41% | −15% |
| D | 75% | 25% | | 2.2 | Below detection limit | N/A | | |
| E | 25% | | 75% | 1 | 5.0 | 2000 | 64% | −42% |
| F | 60 | 40 | | — | — | — | — | — |
| G | 60 | 30 | 10 | — | — | — | — | — |

As shown in Table 2, glucose permeability is more affected than oxygen permeability by changing the characteristics of the hydrophilic component. In these examples, the hydrophilic component is altered by varying the relative amounts of J600 and J900, the latter of which is more hydrophilic than J600 by virtue of its greater molecular weight. Polymer C is an illustration of how these trends can be used to tailor glucose and oxygen permeabilities. This material has the same fractional amount of polysiloxane (PS) therefore maintaining good oxygen permeation. The hydrophilicity of the polymer has been reduced (relative to a J900-PS polymer) by using equimolar amounts of J900 and J600. Because the hydrophilicity has been decreased without compromising the oxygen permeability of the polymer to a great extent, a material with a superior oxygen/glucose permeability ratio is obtained.

Because the temperature of adipose tissue surrounding a subcutaneous glucose sensor could be expected to range from roughly 30 to 40° C., a polymer whose glucose permeability is unaffected by temperature is desirable. Table 2 details the change in glucose permeability (%) observed when cooling the sensor from 37° C. to 27° C. or warming the sensor to 42° C. from 37° C. Interestingly, glucose permeability drops with increasing temperature, whereas oxygen permeability increases with temperature.

The inverse relationship between glucose permeability and temperature is believed to be the result of the known lower critical solution temperature (LCST) of many water-soluble polyethers such as Jeffamine™ 600 and Jeffamine™ 900. The LCST of aqueous solutions of these polymers is manifested by the fact that these polymers are less soluble in water at higher temperatures. Previous data have shown that glucose permeability improves with increasing membrane hydrophilicity. Therefore, if higher temperatures result in a less hydrated membrane due to the LCST characteristics of the polyether segments of the membrane, glucose permeability would also be lessened at higher temperatures.

The data in the table below suggest materials with smaller fractional polyether compositions are less subject to changes in glucose permeability with changes in temperature. Furthermore, polymers with higher Jeffamine™ 900 content in their hydrophilic portion appear to have glucose permeabilities that are less susceptible to changing temperature.

A polymer with greater than 50% PS content would be beneficial due to the increased oxygen permeability and its reduced susceptibility to temperature modulated glucose permeability. However, the decreased hydrophilicity should be offset with the addition of more Jeffamine™ 900 than Jeffamine™ 600, as the former promotes glucose permeability better than the latter and appears to be less sensitive to thermal changes.

Polymer D, 75% PS-25% Jeff 900, did not show any glucose permeability ($O_2$ permeability was not measured). This suggests that the PS content is best kept below about 75%. A material comprising 60% PS and 40% Jeff 900 (F) may offer advantageous properties. Additionally, 60% PS-30% Jeff 900-10% Jeff 600 (G) would be an additional attractive alternative. Other alternatives that should yield similar results include polymers incorporating polyethylene glycol (PEG), polypropylene glycol (PPG), amino-terminated PEG or PPG, as well as polymeric blends of the polymers incorporating the above components, block copolymers generated from the above components or blends of the above monomers to yield random copolymeric structures.

In addition to the hydrophilic and hydrophobic polymers described above, the reaction mixture comprises a diisocyanate, which constitutes about 50 mole % of the reaction mixture. Examples of diisocyanates include hexamethylene-1,6-diisocyanate (HMDI), dicyclohexylmethane 4,4'-diisocyanate, and isophorone diisocyanate. In some embodiments, 10% excess HMDI is included in the reaction mixture. In some embodiments, the reaction mixture further comprises a chain extender, such as N-methyl diethanolamine (NMDA), ethylene diamine (EDA) or water ($H_2O$).

Factors useful in selecting a polymeric composition for use in a biocompatible membrane of the invention include hydration rate, diffusion coefficient, and sensor performance and linearity. Preferred compositions have an initial hydration rate (mg/min for a 5 minute period) at least equal to 29, a diffusion coefficient at least equal to $0.82 \times 10^{-6}$ mm h, and sensor performance in 100 mg/dL glucose solution of between 20 and 70 nA (more preferably between 25 and 30 nA) with membrane thickness' (as measured by reflectometry from a gold plated glass slide coated under the same conditions as the sensors) that will allow for increasing coating thickness in the case of high readings, and reducing thickness in the case of low readings.

Biosensor

Biosensors typically include a transducer that generates a signal upon contact with an analyte of interest. For example, glucose sensors suitable for in vivo use can be prepared by depositing a glucose sensitive enzyme, such as glucose oxidase, onto an electrode via an electromotive plating process. The substrate can be applied by immersion of the sensor in a bath comprising glucose oxidase, a stabilizing protein, a surfactant and a buffer for conductivity and stability of the protein solution, and the enzyme is then deposited onto the electrode potentiometrically. Alternatively, the substrate can be applied using a microelectrogravimetric plating method, such as is described in U.S. patent application Ser. No. 09/642,623.

The invention provides an implantable biosensor for measuring an analyte of interest in biological tissue, the biosensor having a coating comprising a biocompatible membrane of the invention. The implantable biosensor can further comprise a transducer that generates a signal upon contact with the analyte. In a preferred embodiment, the analyte is glucose and the transducer is glucose oxidase. Other enzymes can serve as transducers as appropriate for the analyte of interest and examples of such enzymes include, but are not limited to, lactate oxidase, amino acid oxidase, glutathione, and reductase.

Methods

The invention additionally provides a method of measuring an analyte in a tissue of a subject. The method comprises introducing an implantable biosensor of the invention into the tissue of the subject, and detecting the signal generated by the transducer. The amount of signal corresponds to the amount of analyte. Preferably, the analyte is glucose and the transducer is glucose oxidase.

The above description is illustrative and not restrictive. Many variations of the invention will become apparent to those of skill in the art upon review of this disclosure. Merely by way of example a variety of solvents, membrane formation methods, and other materials may be used without departing from the scope of the invention. The scope of the invention should, therefore, be determined not with reference to the above description, but instead should be determined with reference to the appended claims along with their full scope of equivalents. All publications, patents and patent applications mentioned in this specification are herein incorporated by reference into the specification to the same extent as if each individual publication, patent or patent application was specifically and individually indicated to be incorporated herein by reference.

What is claimed is:

1. A biocompatible membrane comprising a hydrophilic polyurea composition comprising the product of a first reaction mixture comprising a chain extender and:
    (a) an amino terminated polysiloxane;
    (b) a hydrophilic polymer selected from the group consisting of a diamino terminated copolymer of polypropylene glycol and polyethylene glycol, polyethylene glycol, polypropylene glycol and diamino polyethylene glycol having an average molecular weight ($M_D$) of from about 900 to about 2000; and
    (c) a diisocyanate selected from the group consisting of hexamethylene-1,6-diisocyanate dicyclohexylmethane 4,4'-diisocyanate, and isophorone diisocyanate, and constituting about 50 mole % of the reaction mixture;
wherein (a) and (b) constitute a polymeric portion of the first reaction mixture, and wherein the hydrophilic polyurea composition has a ratio of its diffusion coefficient for oxygen to its diffusion coefficient for glucose of from greater than 2,000 to about 10,000.

2. The biocompatible membrane of claim 1, wherein the hydrophilic polyurea composition has a ratio of its diffusion coefficient for oxygen to its diffusion coefficient for glucose of from about 3,000 to about 7,000.

3. The biocompatible membrane of claim 1, wherein the hydrophilic polyurea composition has a ratio of its diffusion coefficient for oxygen to its diffusion coefficient for glucose of from about 5,000 to about 7,000.

4. The biocompatible membrane of claim 1, wherein the polysiloxane has a molecular weight of from about 500 to about 3,500.

5. The biocompatible membrane of claim 4, wherein the polysiloxane has a molecular weight of about 2,500.

6. The biocompatible membrane of claim 1, wherein the chain extender is selected from the group consisting of N-methyl diethanolamine, ethylene diamine, butane diol, diethylene glycol, propane diol and water.

7. The biocompatible membrane of claim 1, wherein the mixture has a glucose diffusion coefficient of from about $1 \times 10^{-9}$ cm$^2$/s to about $200 \times 10^{-9}$ cm$^2$/s at 37° C.

8. The biocompatible membrane of claim 1, wherein the mixture has a glucose diffusion coefficient of from about $2.5 \times 10^{-9}$ cm$^2$/s to about $10 \times 10^{-9}$ cm$^2$/s at 37° C.

9. The biocompatible membrane of claim 1, wherein the polysiloxane content is from about 15 mole percent to about 75 mole percent of the polymeric portion of the mixture.

10. The biocompatible membrane of claim 1, wherein the polysiloxane content is about 50 mole percent of the polymeric portion of the mixture.

11. A biocompatible membrane comprising a hydrophilic polyurea composition comprising the product of a first reaction mixture and a second reaction mixture:
wherein the first reaction mixture comprises:
    (a) an amino terminated polysiloxane;
    (b) a hydrophilic polymer selected from the group consisting of a diamino terminated copolymer of polypropylene glycol and polyethylene glycol, polyethylene glycol, polypropylene glycol and diamino polyethylene glycol having an average molecular weight ($M_D$) of from about 900 to about 2000; and
    (c) a diisocyanate selected from the group consisting of hexamethylene-1,6-diisocyanate, dicyclohexylmethane 4,4'-diisocyanate, and isophorone diisocyanate, and constituting about 50 mole % of the reaction mixture;

wherein (a) and (b) constitute a polymeric portion of the first reaction mixture, wherein the second reaction mixture is blended with the polymeric portion of the first reaction mixture and comprises:

(d) an amino terminated polysiloxane; and (e) a hydrophilic polymer selected from the group consisting of a diamino terminated copolymer of polypropylene glycol and polyethylene glycol, polyethylene glycol, polypropylene glycol and diamino polyethylene glycol having an average molecular weight ($M_D$) of from about 400 to about 2000;

and wherein the hydrophilic polyurea composition has a ratio of its diffusion coefficient for oxygen to its diffusion coefficient for glucose of from greater than 2000 to about 10,000.

12. An implantable biosensor for measuring an analyte in biological tissue, the biosensor having a coating adhered thereto, the coating comprising a bio compatible membrane of claim 11.

13. A biocompatible membrane comprising a hydrophilic polyurea composition comprising the product of a first reaction mixture comprising:

(a) an amino terminated polysiloxane;

(b) a hydrophilic polymer comprising a combination of a diamino terminated copolymer of polypropylene glycol and polyethylene glycol having an average molecular weight ($M_D$) of about 600; and a diamino terminated copolymer of polypropylene glycol and polyethylene glycol having an average molecular weight ($M_D$) of about 900; and (c) a diisocyanate selected from the group consisting of hexamethylene-1,6-diisocyanate, dicyclohexylmethane 4,4'-diisocyanate, and isophorone diisocyanate, and constituting about 50 mole % of the reaction mixture;

wherein (a) and (b) constitute polymeric portion of the first reaction mixture, and wherein the hydrophilic polyurea composition has a ratio of its diffusion coefficient for oxygen to its diffusion coefficient for glucose of from greater than 2,000 to about 10,000.

14. The biocompatible membrane of claim 13, wherein the diamino terminated copolymer of polypropylene glycol and polyethylene glycol comprises a poly(propylene glycol)-block-poly(ethylene glycol) bis(2-aminopropyl ether).

15. An implantable biosensor for measuring an analyte in biological tissue, the biosensor having a coating adhered thereto, the coating comprising a biocompatible membrane of claim 13.

16. A biocompatible membrane comprising a hydrophilic polyurea composition comprising the product of a first reaction mixture comprising:

(a) an amino terminated polysiloxane;

(b) a hydrophilic polymer selected from the group consisting of a diamino terminated copolymer of polypropylene glycol and polyethylene glycol, polyethylene glycol, polypropylene glycol and diamino polyethylene glycol having an average molecular weight ($M_D$) of from about 900 to about 2000; and (c) a diisocyanate selected from the group consisting of hexamethylene-1,6-diisocyanate, dicyclohexylmethane 4,4'-diisocyanate, and isophorone diisocyanate, and constituting about 50 mole % of the reaction mixture;

wherein (a) and (b) constitute a polymeric portion of the first reaction mixture;

wherein the polymeric portion of the mixture comprises about 50 mole percent polysiloxane, about 25 mole percent hydrophilic polymer having an average molecular weight ($M_D$) of about 600, and about 25 mole percent hydrophilic polymer having an average molecular weight ($M_D$) of about 900; and wherein the hydrophilic polyurea composition has a ratio of its diffusion coefficient for oxygen to its diffusion coefficient for glucose of from greater than 2000 to about 10,000.

17. The biocompatible membrane of claim 16, wherein the hydrophilic polymer comprises a diamino terminated copolymer of polypropylene glycol and polyethylene glycol.

18. The biocompatible membrane of claim 17, wherein the diamino terminated copolymer of polypropylene glycol and polyethylene glycol comprises a poly(propylene glycol-block-poly(ethylene glycol) bis(2-aminopropyl ether).

19. An implantable biosensor for measuring an analyte in biological tissue, the biosensor having a coating adhered thereto, the coating comprising a biocompatible membrane of claim 16.

20. An implantable biosensor for measuring an analyte in biological tissue, the biosensor having a coating adhered thereto, the coating comprising a biocompatible membrane comprising a hydrophilic polyurea composition comprising the product of a first reaction mixture comprising:

(a) an amino terminated polysiloxane;

(b) a hydrophilic polymer selected from the group consisting of a diamino terminated copolymer of polypropylene glycol and polyethylene glycol, polyethylene glycol, polypropylene glycol and diamino polyethylene glycol having an average molecular weight ($M_D$) of from about 900 to about 2000; and (c) a diisocyanate selected from the group consisting of hexamethylene-1,6-diisocyanate, dicyclohexylmethane 4,4'-diisocyanate, and isophorone diisocyanate, and constituting about 50 mole % of the reaction mixture;

wherein (a) and (b) constitute a polymeric portion of the first reaction mixture, and wherein the hydrophilic polyurea composition has a ratio of its diffusion coefficient for oxygen to its diffusion coefficient for glucose of from greater than 2,000 to about 10,000.

21. The implantable biosensor of claim 20, further comprising a transducer that generates a signal upon contact with the analyte.

22. The implantable biosensor of claim 21, wherein the analyte is glucose and the transducer is glucose oxidase.

23. A method of measuring an analyte in a tissue of a subject, the method comprising introducing an implantable biosensor of claim 21 into the tissue of the subject and detecting the signal generated by the transducer, wherein the amount of signal corresponds to the amount of analyte.

24. The method of claim 23, wherein the analyte is glucose and the transducer is glucose oxidase.

25. A biocompatible membrane comprising a hydrophilic polyurea composition comprising the product of a first reaction mixture comprising:

(a) an amino terminated polysiloxane;

(b) a hydrophilic polymer comprising a poly(propylene glycol)-block-poly(ethylene glycol) bis(2-aminopropyl ether); and (c) a diisocyanate selected from the group consisting of hexamethylene-1,6-diisocyanate, dicyclohexylmethane 4,4'-diisocyanate, and isophorone diisocyanate, and constituting about 50 mole % of the reaction mixture;

wherein (a) and (b) constitute a polymeric portion of the first reaction mixture, and wherein the hydrophilic polyurea composition has a ratio of its diffusion coefficient for oxygen to its diffusion coefficient for glucose of from greater than 2,000 to about 10,000.

26. The biocompatible membrane of claim 25, wherein the hydrophilic polyurea composition further comprises a second reaction mixture, wherein the second reaction mixture is blended with the polymeric portion of the first reaction mixture and comprises:

(d) an amino terminated polysiloxane; and (e) a hydrophilic polymer selected from the group consisting of a diamino terminated copolymer of polypropylene glycol and polyethylene glycol, polyethylene glycol, polypropylene glycol and diamino polyethylene glycol having an average molecular weight ($M_D$) of from about 400 to about 2000.

27. An implantable biosensor for measuring an analyte in biological tissue, the biosensor having a coating adhered thereto, the coating comprising a biocompatible membrane of claim 25.

28. A method of measuring an analyte in a tissue of a subject, the method comprising introducing an implantable biosensor of claim 27 into the tissue of the subject and detecting the signal generated by the transducer, wherein the amount of signal corresponds to the amount of analyte.

29. A biocompatible membrane comprising a hydrophilic polyurea composition comprising the product of a first reaction mixture and a second reaction mixture, the first reaction mixture comprising:

(a) an amino terminated polysiloxane;

(b) a hydrophilic polymer selected from the group consisting of a diamino terminated copolymer of polypropylene glycol and polyethylene glycol, polyethylene glycol, polypropylene glycol and diamino polyethylene glycol having an average molecular weight ($M_D$) of from about 400 to about 2000; and (c) a diisocyanate selected from the group consisting of hexamethylene-1,6-diisocyanate, dicyclohexylmethane 4,4'-diisocyanate, and isophorone diisocyanate, and constituting about 50 mole % of the reaction mixture;

wherein (a) and (b) constitute a polymeric portion of the first reaction mixture, wherein the second reaction mixture is blended with the polymeric portion of the first reaction mixture and comprises:

(d) an amino terminated polysiloxane; and (e) a hydrophilic polymer selected from the group consisting of a diamino terminated copolymer of polypropylene glycol and polyethylene glycol, polyethylene glycol, polypropylene glycol and diamino polyethylene glycol having an avenge molecular weight ($M_D$) of from about 400 to about 2000, wherein the polysiloxane content is about 50 mole percent of the polymeric portion of the mixture, and wherein the hydrophilic polyurea composition has a ratio of its diffusion coefficient for oxygen to its diffusion coefficient for glucose of from greater than 2,000 to about 10,000.

30. An implantable biosensor for measuring an analyte in biological tissue, die biosensor having a coating adhered thereto, the coating comprising a biocompatible membrane comprising a hydrophilic polyurea composition comprising the product of a first reaction mixture comprising:

(a) an amino terminated polysiloxane;

(b) a hydrophilic polymer selected from the group consisting of a diamino terminated copolymer of polypropylene glycol and polyethylene glycol, polyethylene glycol, polypropylene glycol and diamino polyethylene glycol having an average molecular weight ($M_D$) of from about 400 to about 2000; and (c) a diisocyanate selected from the group consisting of hexamethylene-1,6-diisocyanate, dicyclohexylmethane 4,4'-diisocyanate, and isophorone diisocyanate, and constituting about 50 mole % of the reaction mixture;

wherein (a) and (b) constitute a polymeric portion of the first reaction mixture, wherein the polysiloxane content is about 50 mole percent of the polymeric portion of the mixture, and wherein the hydrophilic polyurea composition has a ratio of its diffusion coefficient for oxygen to its diffusion coefficient for glucose of from greater than 2,000 to about 10,000.

31. A method of measuring an analyte in a tissue of a subject the method comprising introducing an implantable biosensor of claim 30 into the tissue of the subject and detecting the signal generated by the transducer, wherein the amount of signal corresponds to the amount of analyte.

* * * * *

UNITED STATES PATENT AND TRADEMARK OFFICE
CERTIFICATE OF CORRECTION

PATENT NO. : 6,642,015 B2
DATED : November 4, 2003
INVENTOR(S) : David J. Vachon, Brooks B. Cochran and Bill C. Ponder It is certified that error appears in the above-identified patent and that said Letters Patent is hereby corrected as shown below:

Column 12,
Line 13, 62, "$(M_D)$" should read -- $(M_r)$ --.

Column 13,
Lines 11, 27, 29 and 58, "$(M_D)$" should read -- $(M_r)$ --.
Line 18, "bio compatible" should read -- biocompatible --.

Column 14,
Lines 2, 3 and 29, "$(M_D)$" should read -- $(M_r)$ --.

Column 15,
Lines 11 and 31, "$(M_D)$" should read -- $(M_r)$ --.

Column 16,
Lines 6 and 24, "$(M_D)$" should read -- $(M_r)$ --.

Signed and Sealed this

Sixteenth Day of March, 2004

JON W. DUDAS
*Acting Director of the United States Patent and Trademark Office*